(12) United States Patent
Miyawaki et al.

(10) Patent No.: US 7,981,658 B2
(45) Date of Patent: Jul. 19, 2011

(54) NUCLEIC ACID MOLECULES, VECTORS, AND HOST CELLS ENCODING FLUORESCENT PROTEIN

(75) Inventors: Atsushi Miyawaki, Wako (JP); Takeharu Nagai, Tokyo (JP)

(73) Assignee: Riken, Wako-shi (JP)

( * ) Notice: Subject to any disclaimer, the term of this patent is extended or adjusted under 35 U.S.C. 154(b) by 0 days.

(21) Appl. No.: 12/569,464

(22) Filed: Sep. 29, 2009

(65) Prior Publication Data

US 2010/0184116 A1 Jul. 22, 2010

Related U.S. Application Data

(62) Division of application No. 10/162,593, filed on Jun. 6, 2002, now Pat. No. 7,595,375.

(30) Foreign Application Priority Data

Jun. 8, 2001 (JP) ................................. 2001-174421

(51) Int. Cl.
*C12N 1/20* (2006.01)
*C12N 15/00* (2006.01)
*C07K 1/00* (2006.01)
*C07H 21/04* (2006.01)

(52) U.S. Cl. .................. 435/252.3; 435/320.1; 530/350; 536/23.2

(58) Field of Classification Search ........................ None
See application file for complete search history.

(56) References Cited

U.S. PATENT DOCUMENTS

| | | |
|---|---|---|
| 4,314,936 A | 2/1982 | Yaron et al. |
| 4,868,103 A | 9/1989 | Stavrianopoulos et al. |
| 5,070,012 A | 12/1991 | Nolan et al. |
| 5,134,232 A | 7/1992 | Tsien et al. |
| 5,264,563 A | 11/1993 | Huse |
| 5,283,173 A | 2/1994 | Fields et al. |
| 5,439,797 A | 8/1995 | Tsien et al. |
| 5,491,084 A | 2/1996 | Chalfie et al. |
| 5,599,906 A | 2/1997 | Dasmahapatra |
| 5,602,021 A | 2/1997 | Davis et al. |
| 5,605,809 A | 2/1997 | Komoriya et al. |
| 5,614,191 A | 3/1997 | Puri et al. |
| 5,624,048 A | 4/1997 | Sander et al. |
| 5,625,048 A | 4/1997 | Tsien et al. |
| 5,741,668 A | 4/1998 | Ward et al. |
| 5,777,079 A | 7/1998 | Tsien et al. |
| 5,795,737 A | 8/1998 | Seed et al. |
| 5,804,387 A | 9/1998 | Cormack et al. |
| 5,958,713 A | 9/1999 | Thastrup et al. |
| 5,968,738 A | 10/1999 | Anderson et al. |
| 5,981,200 A | 11/1999 | Tsien et al. |
| 5,994,077 A | 11/1999 | Valdivia et al. |
| 5,998,204 A | 12/1999 | Tsien et al. |
| 6,027,881 A | 2/2000 | Pavlakis et al. |
| 6,054,321 A | 4/2000 | Tsien et al. |
| 6,066,476 A | 5/2000 | Tsien et al. |
| 6,077,707 A | 6/2000 | Tsien et al. |
| 6,124,128 A | 9/2000 | Tsien et al. |
| 6,140,132 A | 10/2000 | Tsien et al. |
| 6,146,826 A | 11/2000 | Chalfie et al. |
| 6,172,188 B1 | 1/2001 | Thastrup et al. |
| 6,197,928 B1 | 3/2001 | Tsien et al. |
| 6,319,669 B1 | 11/2001 | Tsien et al. |
| 6,403,374 B1 | 6/2002 | Tsien et al. |
| 6,593,135 B2 | 7/2003 | Wachter et al. |
| 6,638,732 B1 | 10/2003 | Evans |
| 6,780,975 B2 | 8/2004 | Tsien et al. |
| 6,800,733 B2 | 10/2004 | Tsien et al. |
| 6,803,188 B1 | 10/2004 | Tsien et al. |
| 7,060,869 B2 | 6/2006 | Tsien et al. |
| 7,166,424 B2 | 1/2007 | Michnick et al. |
| 2002/0164674 A1 | 11/2002 | Tsien et al. |
| 2005/0079525 A1 | 4/2005 | Tsien et al. |
| 2006/0112440 A1 | 5/2006 | Tsien et al. |
| 2007/0021598 A1 | 1/2007 | Evans |

FOREIGN PATENT DOCUMENTS

| | | |
|---|---|---|
| EP | 0 428 000 A1 | 5/1991 |
| EP | 1 104 769 A2 | 6/2001 |
| EP | 1 238 982 A1 | 9/2002 |
| WO | WO 91/01305 A1 | 2/1991 |
| WO | WO 94/28166 A1 | 12/1994 |
| WO | WO 94/28173 A1 | 12/1994 |
| WO | WO 95/07463 A1 | 3/1995 |
| WO | WO 95/21191 A1 | 8/1995 |
| WO | WO 96/13607 A1 | 5/1996 |
| WO | WO 96/23810 A1 | 8/1996 |
| WO | WO 96/23898 A1 | 8/1996 |
| WO | WO 96/27027 A1 | 9/1996 |
| WO | WO 96/27675 A1 | 9/1996 |
| WO | WO 97/11094 A1 | 3/1997 |
| WO | WO 97/26333 A1 | 7/1997 |
| WO | WO 97/28261 A1 | 8/1997 |

(Continued)

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Angleson et al., *Trends Neurosci.*, 20: 281-287 (1997).
Anderson et al., *Proc. Natl. Acad. Sci. U.S.A.*, 93(16): 8508-8511 (1996).
Baldwin et al., *Biochemistry*, 29: 5509-5515 (1990).
Blondel, *Protein Engineering*, 4(4): 457-461 (1991).
Bouvier et al., *Methods in Enzymology*, 248: 614-633 (1995).
Cadwell et al., *PCR Methods and Applications*, 3: S136-S140 (1994).
Cartwright et al., *Yeast*, 10: 497-508 (1994).
Cesare et al., *Ann. New York Acad. Sci.*, 976: 520-527 (2002).
Chalfie et al., *Science*, 263: 802-805 (1994).

(Continued)

*Primary Examiner* — Christian Fronda
(74) *Attorney, Agent, or Firm* — Leydig, Voit & Mayer, Ltd.

(57) ABSTRACT

The present invention provides a fluorescent protein having an amino acid sequence of the green fluorescent protein, the yellow fluorescent protein or mutants thereof wherein the 46$^{th}$ phenylalanine residue is substituted with a leucine residue. According to the present invention, there are provided novel GFP or YEP mutants having an excellent maturation efficacy and having a decreased sensitivity to both of $H^+$ and $Cl^{31}$.

22 Claims, 4 Drawing Sheets

FOREIGN PATENT DOCUMENTS

| | | |
|---|---|---|
| WO | WO 97/42320 A1 | 11/1997 |
| WO | WO 98/02571 A1 | 1/1998 |
| WO | WO 98/06737 A1 | 2/1998 |
| WO | WO 98/14605 A1 | 4/1998 |
| WO | WO 98/40477 A1 | 9/1998 |
| WO | WO 98/47148 A2 | 10/1998 |
| WO | WO 99/64592 A2 | 12/1999 |
| WO | WO 01/90147 A2 | 11/2001 |
| WO | WO 01/98338 A1 | 12/2001 |
| WO | WO 02/085936 A1 | 10/2002 |

OTHER PUBLICATIONS

Chalfie, *Photochemistry and Photobiology*, 62(4): 651-656 (1995).
Chattoraj et al., *Proc. Natl. Acad. Sci. U.S.A.*, 93: 8362-8367 (1996).
Cheng et al., *Nature Biotechnology*, 14: 606-609 (1996).
Cody et al., *Biochemistry*, 32: 1212-1218 (1993).
Colbran et al., *J. Biol. Chem.*, 267: 9589-9594 (1992).
Crameri et al., *Nature Biotechnol.*, 14: 315-319 (1996).
Cubitt et al., *Trends in Biochem. Science*, 20: 448-455 (1995).
Cubitt et al., *Methods in Cell Biology*, 58: 19-30 (1999).
Delagrave et al., *Biotechnology*, 11: 1548-1552 (1993).
Delagrave et al., *Biotechnology*, 13: 151-154 (1995).
Deschamps et al., *Protein Expression and Purification*, 6: 555-558 (1995).
Dickson et al., *Science*: 274, 966-969 (1996).
Dopf et al., *Gene*, 173: 39-44 (1996).
Dunn et al., *Methods in Enzymology*, 241: 254-279 (1994).
Ehrig et al., *FEBS Letters*, 367: 163-166 (1995).
Elsliger et al., *Biochemistry*, 38: 5296-5301 (1999).
Geoghegan et al., *Bioconjugate Chem.*, 4: 537-544 (1993).
Giuliano et al., *Annual Review of Biophysics and Biomolecular Structure*, 24: 405-434 (1995).
Graff et al., *The Journal of Biological Chemistry*, 266(2): 14390-14398 (1991).
Griesbeck et al., *J. Biol. Chem.*, 276(31): 29188-29194 (2001).
Guo et al., *Proc. Natl. Acad. Sci. U.S.A.*, 101: 9205-9210 (2004).
Hardy et al., "Generic Variability and Alzheimer's Disease," *Amyloid Protein Precursor in Development, Aging and Alzheimer's Disease*, 190-198 (1994).
Heikal et al., *Proc. Natl. Acad. Sci. U.S.A.*, 97(22): 11996-12001 (2000).
Heim et al., *Biochemistry*, 91: 12501-12504 (1994).
Heim et al., *Nature*, 373: 663-664 (1995).
Heim et al., *Current Biology*, 6(2): 178-182 (1996).
Houdebine, *J. Biotech.*, 34: 269-287 (1994).
Inouye et al., *FEBS Letters*, 341: 277-280 (1994).
Jayaraman et al., *J. Biol. Chem.*, 275(9): 6047-6050 (2000).
Kain et al., *BioTechniques*, 19(4): 650-655 (1995).
Kappel et al., *Current Opinion in Biotechnology*, 3(5): 548-553 (1992).
Kemp et al., *TIBS*, 15: 342-346 (1990)
Kilgard et al., *Nature*, 373: 663-664 (1995).
Knight, *Methods in Enzymology*, 248: 18-34 (1995).
Kolberg, *Journal of NIH Research*, 5: 44-47 (1994).
Krafft et al., *Methods in Enzymology*, 241: 70-86 (1994).
Kuner et al., *Neuron*, 27: 447-459 (2000).
Lang et al., *Neuron*, 18: 857-863 (1997).
Lee et al., *Proc. Natl. Acad. Sci. U.S.A.*, 91: 6413-6417 (1994).
Levine et al., *Comparative Biochemistry and Physiology*, 72B(1): 77-85 (1982).
Marshall et al., *Neuron*, 14: 211-215 (1995).
Matayoshi et al., *Science*, 247: 954-958 (1990).
Misteli et al., *Nature Biotechnology*, 15: 961-964 (1997).
Mitra et al., *Gene*, 173: 13-17 (1996).
Miyawaki et al., *Nature*, 388: 882-887 (1997).
Miyawaki et al., *Proc. Natl. Acad. Sci. U.S.A.*, 96: 2135-2140 (1999).
Miyawaki et al., *Methods in Enzymology*, 327: 472-500 (2000).
Muhlrad et al., *Yeast*, 8: 79-82 (1992).
Mullins et al., *J. Clin. Invest.*, 97(7): 1557-1560 (1996).
Mullins et al., *J. Clin. Invest.*, 98(11): S37-S40 (1996).
Murray, *Theriogenol.*, 51(1): 149-159 (1999).
Nagai et al., *Proc. Natl. Acad. Sci. U.S.A.*, 98(6): 3197-3202 (2001).
Nagai et al., *Nature Biotechnology*, 20: 87-90 (2002).
Niwa et al., *Proc. Natl. Acad. Sci. U.S.A.*, 93: 13617-13622 (1996).
Norris et al., *Plant Molecular Biology*, 24: 673-677 (1994).
Ormo et al., *Science*, 273: 1392-1395 (1996).
Palm et al., *Nature Struct. Biol.*, 4: 361-365 (1997).
Perozzo et al., *J. Biol. Chem.*, 263(16): 7713-7716 (1988).
Pouli et al., *Biochem J.*, 331: 669-675 (1998).
Prasher et al., *Gene*, 111: 229-233 (1992).
Reid et al., *Biochemistry*, 36: 6786-6791 (1997).
Sawano et al., *Nucl. Acids Res.*, 28(16): e78 (2000).
Seidah et al., *Methods in Enzymology*, 244: 175-188 (1994).
Sigmund, *Arterioscler. Thromb. Vasc. Biol.*, 20(6); 1425-1429 (2000).
Smith et al., *Methods in Enzymology*, 244: 412-423 (1994).
Songyang et al., *Current Biology*, 4(11): 973-982 (1994).
Stearns, *Current Biology*, 5: 262-264 (1995).
Steyer et al., *Nature Reviews Mol. Cell Biol.*, 2: 268-275 (2001).
Stokoe et al., *Biochemical Journal*, 296: 843-849 (1993).
Stryer, *Annual Review of Biochemistry*, 47: 819-846 (1978).
Thornberry, *Methods in Enzymology*, 244: 615-631 (1994).
Tsien et al., *Trends in Cell Biology*, 3: 242-245 (1993).
Tsien, *Annu. Rev. Biochem.*, 67: 509-544 (1998).
Tsuboi et al., *Current Biology*, 10(20): 1307-1310 (2000).
Wacther et al., *Biochemistry*, 36: 9759-9765 (1997).
Wachter et al., *Structure*, 6, 1267-1277 (1998).
Wachter et al., *Current Biology*, 9(17): R628-R629 (1999).
Wachter et al., *J. Mol. Biol.*, 301: 157-171 (2000).
Wall, *Theriogenol.*, 45: 57-68 (1996).
Wall et al., *J. Dairy Sci.*, 80: 2213-2224 (1997).
Wang et al., *Nature*, 369: 400-403 (1994).
Ward, "Properties of the Coelenterate Green-Fluorescent Protein," *Bioluminescence and Chemiluminescence Basic Chemistry and Analytical Applications*, pp. 235-242 (1981).
Ward et al., *Photochem. Photobiol.*, 35: 803-808 (1982).
Ward et al., *Proc. Natl. Acad. Sci. U.S.A.*, 21: 4535-4540 (1982).
Ward et al., *Photochem. Photobiol.*, 27: 389-396 (1978).
Ward et al., *J. Biol. Chem.*, 254(3): 781-788 (1979).
Wilbanks et al., *J. Biol. Chem.*, 268(2): 1226-1235 (1993).
Wood et al., *Journal of Bioluminescence and Chemiluminescence*, 4: 289-301 (1989).
Wu et al., *Analytical Biochemistry*, 218: 1-13 (1994).
Yang et al., *Nature Biotechnol.*, 14: 1246-1251 (1996).
Yaron et al., *Analytical Biochemistry*, 95: 228-235 (1979).
Yokoe et al., *Nature Biotechnol.*, 14: 1252-1256 (1996).
Zolotukhin et al., *J. Virology*, 70: 4646-4654 (1996).

\* cited by examiner

NUCLEIC ACID MOLECULES, VECTORS, AND HOST CELLS ENCODING FLUORESCENT PROTEIN

CROSS-REFERENCE TO RELATED APPLICATION(S)

This application is a divisional of U.S. patent application Ser. No. 10/162,593, which was filed on Jun. 6, 2002, and which has issued as U.S. Pat. 7,595,375.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 11,371 bytes ASCII (Text) file named "705502SequenceListing.txt," created Mar. 25, 2010.

TECHNICAL FIELD

The present invention relates to a novel fluorescent protein which has an improved property. More particularly, the present invention relates to a fluorescent protein obtained by substituting leucine residue for the 46th amino acid in the green fluorescent protein, the yellow fluorescent protein or the mutants thereof, as well as use thereof.

BACKGROUND ART

The green fluorescent protein (GFP) from the jellyfish *Aequorea victoria* has provided a myriad of applications for biological systems (Tsien, R. Y. (1998) Ann. Rev. Biochem. 67, 509-544). Over the last several years, both random and semi-rational mutagenesis have produced GFP variants with new colors, improved folding property, more brightness, and altered pH-sensitivity. Through genetic manipulations, hundreds of proteins have been successfully fused to GFPs to allow monitoring of their expression and trafficking. When GFP or GFP-fusion protein is heterologously expressed at a certain level, the intensity of the fluorescence depends on:
(1) the ultimate brightness of GFP fluorophore, which is limited by the product of extinction coefficient ($\epsilon$) and fluorescence quantum yield ($\Phi$).
(2) the maturation efficiency of newly-synthesized GFP polypeptides.
(3) the extent of quenching of GFP fluorophore by environmental factors.

The yellow fluorescent protein (YFP) is one of the most commonly used GFP variants and has the longest-wavelength emission of all *Aequorea* GFP variants. The $\epsilon$ and $\Phi$ of most YFP variants are within 60,000 to 100,000 $M^{-1}$ $cm^{-1}$ and 0.6 to 0.8, respectively (Tsien, R. Y. (1998) Ann. Rev. Biochem. 67, 509-544). These values are almost comparable to those of common bright fluorophores, such as fluorescein and rhodamine. Therefore, the improvement of the ultimate brightness of YFP seems to have reached its limit.

Newly-synthesized GFP polypeptides need to mature properly before emitting fluorescence. The maturation involves two steps: first, the protein folding into a nearly native conformation, and then, cyclization of an internal tripeptide followed by oxidation. Some of the primary mutations that improve maturation of GFP have been identified (Tsien, R. Y. (1998) Atm. Rev. Biochem. 67, 509-544). For example, F64L/M153T/V163A/S175G are common mutations introduced in many enhanced GFP variants. M153T and S175G are located on the surface of the $\beta$-barrel and are known to enhance the folding efficiency and the stability by reducing surface hydrophobicity and increasing the solubility of the protein. However, no mutation has been clearly identified to facilitate the final oxidation reaction at 37° C., even though such mutations are very desirable since the oxidation step is the rate-limiting step in the whole process of GFP maturation. Although there has been some improvement in the folding efficiency, slow maturation is still one of the biggest problems in the application of GFP variants for visualization and is even more problematic when they are expressed at 37° C. and/or targeted to certain organelles. Therefore, obtaining GFP variants that have better maturation efficiency is very crucial and necessary at this stage.

Among *Aequorea* GFP variants, YFPs are relatively acid sensitive, and uniquely quenched by halide ions, including chloride ($Cl^-$) (Jayaraman, S., et al. (2000) J. Biol. Chem. 275, 6047-6050; Wachter, R. M., et al. (2000) J. Mol. Biol. 301, 157-171). Proton ($H^+$) and $Cl^-$ synergistically affect the charge state of the chromophore of YFP, thereby suppressing the fluorescence. The concentrations of these ions vary among intracellular organelles; there is a significant accumulation of $H^+$ in secretory organelles. In addition, their concentrations change dynamically upon stimulations (Kuner, T. et al (2000) Neuron 27, 447-459). For instance, glutamate and electrical stimulations of hippocampal neurons reduce intracellular pH by about 0.4, and the receptor-mediated $Cl^-$ fluxes occur in olfactory and GABAergic neurons. To let YFP be fully and stably fluorescent in these situations, the mutations that decrease the sensitivity to both $H^+$ and $Cl^-$ are desired.

SUMMARY OF THE INVENTION

An object of the present invention is to prepare GFP or YFP mutants having an excellent maturation efficiency. Another object of the present invention is to prepare GFP or YFP mutants having a decreased sensitivity to both of $H^+$ and $Cl^-$.

In order to achieve the above object, the present inventors have carried out concentrated research and have constructed a novel mutant of YFP. The present inventors demonstrated the benefits of the new variant by targeting it to secretory vesicles of differentiated PC12 cells for efficient monitoring of exocytotic events, and by using it as an acceptor for immediate detection of reliable FRET (fluorescence resonance energy transfer) signals. The fluorescent proteins of the present invention have an improved speed and yield of maturation and resistancy to both $H^+$ and $Cl^-$, and therefore have wider applicability and enable the fluorescence labeling that were previously impossible.

Thus, according to the present invention, there is provided a fluorescent protein having an amino acid sequence of the green fluorescent protein, the yellow fluorescent protein or mutants thereof wherein the 46th phenylalanine residue is substituted with a leucine residue.

Preferably, the 64th phenylalanine residue is substituted with a leucine residue, the 153th methionine residue is substituted with a threonine residue, the 163th valine residue is substituted with a alanine residue, and the 175th serine residue is substituted with a glycine residue in the amino acid sequence of the green fluorescent protein, the yellow fluorescent protein or mutants thereof.

Examples of the fluorescent protein of the present invention include the fluorescent protein having any of the following sequences;
(a) an amino acids sequence shown in SEQ ID NO:1, or
(b) an amino acid sequence having a deletion, substitution and/or addition of one to several amino acids in an amino acid sequence shown in SEQ ID NO:1 and having a fluorescence characteristic that is equivalent to or greater than that of a protein having the amino acid sequence shown in SEQ ID NO:1;

According to another aspect of the present invention, there is provided DNA which encodes the fluorescent protein of the present invention as mentioned above.

According to further another aspect of the present invention, there is provided a recombinant vector having the DNA of the present invention as mentioned above.

According to further another aspect of the present invention, there is provided a transformant having the DNA or the recombinant vector of the present invention as mentioned above.

According to further another aspect of the present invention, there is provided a fused fluorescent protein which is composed of the fluorescent protein of the present invention as mentioned above and another protein.

Preferably, the another protein is a protein which is located within cell, for example a protein which is specific for intracellular organelles.

According to further another aspect of the present invention, there is provided a method for analyzing localization or dynamic situation of a protein in a cell wherein the fused fluorescent protein of the present invention as mentioned above is expressed in the cell.

According to further another aspect of the present invention, there is provided a method for analyzing a physiologically active substance wherein FRET (fluorescence resonance energy transfer) is carried out by using the fluorescent protein of the present invention as mentioned above as an acceptor protein or a donor protein.

According to further another aspect of the present invention, there is provided a kit for analyzing localization of intracellular components and/or analyzing a physiologically active substance, which comprises the fluorescent protein, DNA, the recombinant vector, the transformant or the fused protein of the present invention as mentioned above.

BRIEF DESCRIPTION OF THE DRAWINGS

FIG. 2 shows fluorescence micrographs of PC12 cells expressing NPY-Venus (A and B) and NPY-EGFP (C-F). Low magnification micrographs show that all of the fluorescent cells expressing NPY-Venus produced bright fluorescence in the neuritis (A), whereas the fluorescence of NPY-EGFP was detected in the cytosol or perinuclear region in some cells (C, indicated by arrows). High magnification micrographs of cells with correctly targeted NPY-Venus (B) and NPY-EGFP (D), and with mistargeted MPY-EGFP (E and F), are shown. In typical cells showing correct targeting of NPY-fusion proteins, the green fluorescence (G and J) and re immune-fluorescence (H and K) signals from NPV-Venus and NPY-EGFP, respectively, were detected. Their ration images of green to red are shown in psudo-color for NPY-Venus (1) and NPY-EGFP (L). Scale bar 10 μm.

MODE FOR CARRYING OUT THE INVENTION

The embodiments and methods for carrying out the present invention are described in detail below.

(1) A Fluorescent Protein of the Present Invention

The fluorescent protein of the present invention is characterized in that the 46th phenylalanine residue is substituted with a leucine residue in the amino acid sequence of the green fluorescent protein, the yellow fluorescent protein or mutants thereof.

The term "the green fluorescent protein (GFP), the yellow fluorescent protein (YFP) or mutants thereof" used herein means has a meaning to include all of known green fluorescent proteins and known yellow fluorescent proteins as well as all of their mutants. For example, the gene of the green fluorescent protein has been isolated and its sequence has also been determined (Prasher, D. C. et al. (1992), "Primary structure of the $Aequorea$ victoria green fluorescent protein", Gene 111: 229-233). There have also been numerous reports of amino acid sequences of other fluorescent proteins or their mutants, for example, as described in Roger Y. Tsin, Annu. Rev. Biochem. 1998. 67:509-44 and the literature cited therein.

The green fluorescent protein (GFP), the yellow fluorescent protein (YFP) or mutants thereof include those derived from jellyfish such as $Aequorea$ Victoria.

Examples of GFP, YFP and mutants thereof are mentioned below. The indication of F99S shows that F is substituted with S at the 99th amino acid residue. Other amino acid substitutions are shown by the similar indication method.

Wild Type GFP;
GFP having amino acid mutations of F99S, M153T, and V163A;
GFP having an amino acid mutation of S65T;
GFP having amino acid mutations of F64L and S65T;
GFP having amino acid mutations of S65T, S72A, N149K, M153T, and I167T;
GFP having amino acid mutations of S202F and T2031;
GFP having amino acid mutations of T2031, S72A and Y145F;
GFP having amino acid mutations of S65G, S72A and T203F (YFP);

GFP having amino acid mutations of S65G, S72A and T203H (YFP);

GFP having amino acid mutations of S65G, V68L, S72A and T203Y (EYFP-V68L);

GFP having amino acid mutations of S65G, V68L, Q69K, S72A and T203Y (EYFP-V68L, Q69K);

GFP having amino acid mutations of S65G, S72A and T203Y (EYFP); and

GFP having amino acid mutations of S65G, S72A, K79R and T203Y (YFP);

One example of the amino acid sequences of enhanced green fluorescent protein which is a mutant of the green fluorescent protein is shown in SEQ ID NO.2 of the Sequence Listing of the present specification, and one example of the amino acid sequences of enhanced yellow fluorescent protein which is a mutant of the yellow fluorescent protein is shown in SEQ ID NO.3 of the Sequence Listing of the present specification.

Since Val is inserted between the first amino acid and the second amino acid in the amino acid sequences of SEQ ID NOS. 2 and 3, the 46th phenylalanine residue (Phe) in the naturally occurring fluorescent protein corresponds to the 47th residue in SEQ ID NOS. 2 and 3.

Examples of the fluorescent protein of the present invention include proteins having the amino acid sequences of SEQ ID NO. 2 or 3 wherein the 47th phenylalanine (Phe) residue is substituted with a leucine residue.

In preferred embodiments of the present invention, the 64th phenylalanine residue is substituted with a leucine residue, the 153th methionine residue is substituted with a threonine residue, the 163th valine residue is substituted with a alanine residue, and the 175th serine residue is substituted with a glycine residue in the amino acid sequence of the green fluorescent protein, the yellow fluorescent protein or mutants thereof, in addition to that the 46th phenylalanine residue is substituted with a leucine residue.

As described above, the 64th, 153th, 163th and 175th amino acid residues respectively correspond to the 65th, 154th, 164th and 176th amino acids in the SEQ ID NOS 2 and 3.

Examples of the fluorescent protein of the present invention include the fluorescent protein having any of the following amino acid sequences;
(a) an amino acids sequence shown in SEQ ID NO:1, or
(b) an amino acid sequence having a deletion, substitution and/or addition of one to several amino acids in an amino acid sequence shown in SEQ ID NO:1 and having a fluorescence characteristic that is equivalent to or greater than that of a protein having the amino acid sequence shown in SEQ ID NO:1;

In the term "an amino acid sequence having a deletion, substitution and/or addition of one to several amino acids" used in the present specification, the range of "one to several" is not particularly limited, but is, for example, from 1 to 20, preferably 1 to 10, more preferably 1 to 7, still more preferably 1 to 5, and particularly preferably 1 to 3.

The term "having a fluorescence characteristic that is equivalent to or greater than" is used herein to mean that the protein has an equivalent or greater fluorescent intensity, an equivalent wave length, an equivalent or greater maturation speed and maturation efficacy, and an equivalent or lower sensitivity to $H^+$ and $Cl^-$.

The method for obtaining the fluorescent protein of the present invention is not particularly limited. There may be used any of a chemically synthesized protein, or a recombinant protein produced by a gene recombination technique.

In the case of producing a recombinant protein, it is necessary to obtain the DNA encoding the protein. By utilizing the information of the amino acid sequences shown in SEQ ID NOS:1-3 and the nucleotide sequences (which are examples of the nucleotide sequences encoding the amino acid sequences of SEQ ID NOS:2 and 3) shown in SEQ ID NOS:4 and 5 of the sequence list herein, suitable primers can be designed, and by using those to perform PCR using a cDNA clone of various known fluorescent proteins as described above as a template, DNA encoding the fluorescent protein of the present invention can be prepared. When partial fragment of DNA encoding the fluorescent protein of the present invention was obtained by the aforementioned PCR, DNA encoding the desired fluorescent protein can be obtained by ligating those DNA fragments in order by means of a gene recombination technique. A fluorescent protein of the present invention can be produced by introducing this DNA into a suitable expression system. Expression in the expression system is described later in the present specification.

(2) DNA of the Present Invention

The present invention provides a gene encoding the fluorescent protein of the present invention.

Examples of DNA encoding the fluorescent protein of the present invention include any of the following DNA.
(a) DNA which encodes the amino acid sequence shown in SEQ ID NO:1;
(b) DNA which encodes the amino acid sequence having a deletion, substitution and/or addition of one to several amino acids in an amino acid sequence shown in SEQ ID NO:1 and having a fluorescence characteristic that is equivalent to or greater than that of a protein having the amino acid sequence shown in SEQ ID NO:1.

The DNA of the present invention can, for example, be synthesized by the phosphoramidite method or the like, and can be produced by polymerase chain reaction (PCR) using specific primers. The method of preparation of the DNA of the present specification or its fragments is as described herein above.

Further, a method for introducing a desired mutation into certain nucleotide sequence is known to persons skilled in the art. For example, it is possible to construct DNA having a mutation by suitably using a known technique such as site-directed mutagenesis, PCR using a degenerate oligonucleotide, exposure of a cell which contains nucleic acid to a mutagenetic agent or radiation, or the like. Such known techniques are described in, for example, Molecular Cloning: A laboratory Manual, $2^{nd}$ Ed., Cold Spring Harbor Laboratory, Cold Spring Harbor, N.Y., 1989, and Current Protocols in Molecular Biology, Supplement 1-38, John Wiley & Sons (1987-1997).

(3) The Recombinant Vector of the Present Invention

The DNA of the present invention can be used after insertion into a suitable vector. The types of vectors used in the present invention are not particularly limited. For example, the vector may be a vector which replicates autonomously (for example, a plasmid), or may be a vector which is integrated into the genome of the host cell when introduced into the host cell and is replicated along with the chromosome.

Preferably, the vector used in the present invention is an expression vector. In an expression vector, elements necessary for transcription (for example, a promoter and the like) are operatively linked to the DNA of the present invention. A promoter is a DNA sequence which exhibits transcription activity in a host cell, and the promoter can be suitably selected in accordance with the type of host.

Examples of promoters which are operative in bacterial cells include, a promoter of *Bacillus stearothermophilus* maltogenic amylase gene, *Bacillus licheniformis* alpha-amylase gene, *Bacillus amyloliquefaciens* BAN amylase gene, *Bacillus subtilis* alkaline protease gene, or *Bacillus pumilus* xylosidase gene; a $P_R$ or $P_L$ promoter of phage lambda; a lac, trp, or tac promoter of *Escherichia coli*; and the like.

Examples of promoters which are operative in mammalian cells include SV40 promoter, MT-1 (metallothionein gene) promoter, adenovirus 2 major late promoter, and the like. Examples of promoters which are operative in insect cells include polyhedrin promoter, P10 promoter, basic protein promoter of *Autographa californica* nuclear polyhedrosis, baculovirus immediate early gene 1 promoter, baculovirus 39K delayed early gene promoter, and the like. Examples of promoters which are operative in yeast host cells include a promoter derived from yeast glycolysis system genes, alcohol dehydrogenase gene promoter, TPI1 promoter, ADH2-4c promoter, and the like.

Examples of promoters which are operative in mycotic cells include ADH3 promoter, tpiA promoter, and the like.

Further, if necessary, the DNA of the present invention may be operatively linked to a suitable terminator, such as a human growth hormone terminator, or TPI1 terminator or ADH3 terminator for a fungal host. The recombinant vector of the present invention may also have an element such as a polyadenylation signal (for example, one derived from SV40 or the adenovirus 5E1b region), a transcription enhancer sequence (for example, SV40 enhancer), or a translation enhancer sequence (for example, one encoding adenovirus VA RNA).

The recombinant vector of the present invention may also be provided with a DNA sequence which enables the vector to replicate inside the host cell, and an example thereof is an SV40 origin of replication (when the host cell is a mammalian cell).

The recombinant vector of the present invention may also contain a selectable marker. Examples of a selectable marker include genes whose complement is absent in the host cell such as dihydrofolate reductase (DHFR) or *schizosaccharomyces pombe* TPI gene, or drug resistance genes such as ampicillin, kanamycin, tetracycline, chloramphenicol, neomycin, and hygromycin.

A method for connecting the DNA of the present invention, a promoter, and, as desired, a terminator and/or a secretion signal sequence, respectively, and inserting these into a suitable vector is known to persons skilled in the art.

(4) A Transformant of the Present Invention

A transformant can be produced by introducing the DNA or recombinant vector of the present invention into a suitable host.

A host cell into which the DNA or recombinant vector of the present invention is introduced may be any cell which can express the DNA construct of the present invention, and examples include bacteria, yeast, fungi, and higher eukaryotic cells.

Examples of bacterial cells include Gram-positive bacteria such as *Bacillus* and *Streptomyces*, and Gram-negative bacteria such as *Escherichia coli*. Transformation of these bacteria may be performed by the protoplast method or a known method using competent cells.

Examples of mammalian cells include HEK293 cell, HeLa cells, COS cell, BHK cell, CHL cell, and CHO cell. Methods for transforming a mammalian cell and expressing the DNA sequence inserted into the cell are known. For example, methods such as electroporation, phosphate calcium method, or lipofection can be used.

Examples of yeast cells include cells belonging to *Saccharomyces* or *Schizosaccharomyces*, and examples include *Saccharomyces cerevisae* and *Saccharomyces kluyveri*. Examples of methods for introducing a recombinant vector to a yeast host include electroporation, the spheroplast method, and the lithium acetate method.

Other examples of fungal cells are filamentous fungi, for example, *Aspergillus, Neurospora*, and *Fusarium*, and cells belonging to *Trichoderma*. When a filamentous fungus is used as a host cell, transformation can be performed by integrating the DNA construct into the host chromosome and obtaining a recombinant host cell. Integration of the DNA construct into the host chromosome can be performed according to a known method such as homologous recombination or heterologous recombination.

When an insect cell is used as a host, a protein can be expressed by co-transfecting a recombinant gene transduction vector and a baculovirus into the insect cell to obtain a recombinant virus in the insect cell culture supernatant, and then infecting the recombinant virus into the insect cell (for example, as described in Baculovirus Expression Vectors, A Laboratory Manual, and Current Protocols in Molecular Biology, Bio/Technology, 6, 47 (1988), and the like).

As a baculovirus, for example, *Autographa californica* nuclear polyhedrosis virus, which is a virus that infects *Mamestra*-family insects, and the like, can be used.

As an insect cell, for example, Sf9 and Sf21, which are ovarian cells of *Spodoptera frugiperda* [Baculovirus Expression Vectors, A Laboratory Manual, W.H. Freeman and Company, New York, (1992)], and Hi Five, which is an ovarian cell of *Trichoplusia ni* (Invitrogen), or the like can be used.

Examples of a method for co-transfection of a recombinant gene transduction vector and the above-described baculovirus into an insect cell for producing a recombinant virus, include phosphate calcium method or lipofection.

The above-described transformant is cultured in a suitable nutrient culture medium under conditions which enable expression of the introduced DNA construct. To isolate and purify a fluorescent fused protein of the present invention from the culture of the transformant, a conventional method for isolating and purifying a protein may be used.

For example, in a case where a protein of the present invention was expressed in a solubilized form within cells, after culturing is completed, cells are recovered by centrifugation and suspended in a water-based buffer, then a cell-free extract is obtained by disrupting the cells by means of an ultrasonic homogenizer or the like. From the supernatant obtained by centrifuging the cell-free extract, a purified sample can be obtained using a conventional method for isolating and purifying a protein. Examples of the conventional method for isolating and purifying a protein include the use of, either alone or in combination, techniques such as solvent extraction, salting-out by ammonium sulfate or the like, desalting, precipitation by an organic solvent, anion exchange chromatography using a resin such as Diethylaminoethyl (DEAE) Sepharose, cation exchange chromatography using a resin such as S-Sepharose (Pharmacia), hydrophobic chromatography using a resin such as Butyl Sepharose or Phenyl Sepharose, gel filtration using a molecular sieve, affinity chromatography, chromatofocusing, an electrophoresis method such as isoelectric focusing, and the like.

(5) A Fused Fluorescent Protein Comprising the Fluorescent Protein of the Present Invention, and its Use A fused fluorescent protein can be constructed by fusing the fluorescent protein of the present invention with another protein. The kinds of "another protein" to be fused with the fluorescent protein of the present invention are not particularly limited. Example thereof is a protein which is located within cell, more particularly, a protein which is specific for intracellular organelles.

The method for obtaining the fused fluorescent protein of the present invention is not particularly limited. There may be used any of a chemically synthesized protein, or a recombinant protein produced by a gene recombination technique.

In the case of producing a recombinant protein, it is necessary to obtain the DNA encoding the protein. By utilizing the information of the amino acid sequences shown in SEQ ID NOS:1-3 and the nucleotide sequences shown in SEQ ID NOS:4 and 5 of the sequence list herein, suitable primers can be designed, and by using those to perform PCR using a cDNA clone of various known fluorescent proteins as described above as a template, DNA fragments which is necessary for constructing DNA encoding the fluorescent protein of the present invention can be prepared. Further, DNA fragment encoding a protein to be fused is also obtained in the same manner.

Then, DNA encoding the desired fused fluorescent protein can be obtained by ligating those DNA fragments in order by means of a gene recombination technique. A fused fluorescent protein of the present invention can be produced by introducing this DNA into a suitable expression system.

By expressing the fused fluorescent protein obtained by fusing the fluorescent protein of the present invention with another protein (referred to as "protein X") as mentioned above in cells and monitoring the emitted fluorescence, the localization and dynamic situation of protein X in the cell can be analyzed. Thus, by observing a cell which was transformed or transfected with DNA encoding the fused fluorescent protein of the present invention by means of a fluorescent microscope, the localization and dynamic situation of protein X in the cell can be visualized and analyzed.

For example, by using a protein which is specific for intracellular organelles as protein X, distribution and movement of nucleus, mitochondrion, endoplasmic reticulum, secretory vesicles, peroxisome and the like can be observed.

Moreover, since axon and dendroid axon of nerve cells show very complicated change of running direction in developing individuals, dynamic analysis can be carried out by labeling such sites with a fluorescence.

The types of the microscope can be suitably selected depending on the purpose. If frequent observations are necessary for monitoring a time course of the changing, conventional incident-light fluorescent microscope is preferred. If resolution is to be increased as in the case where detailed intracellular localization is to be monitored, confocal laser microscope is preferred. A microscope system, an inverted microscope is preferred in view of keeping the physiological state of cell and preventing contamination. When erecting microscope is used, an immersion lens can be used in the case of using lens of higher power.

The filter set can be suitably selected depending on the fluorescent wave length of the fluorescent protein. For the observation of GFP, it is preferred to use a filter with excitation light of about 470-490 nm and fluorescent light of about 500-520 nm. For the observation of YFP, it is preferred to use a filter with excitation light of about 480-500 nm and fluorescent light of about 510-550 nm.

Moreover, when time course observation is carried out in living cells by using a fluorescent microscope, the cells should be photographed in a short period, and therefore a high sensitive cooled CCD camera is used. By using a cooled CCD camera, thermal noise can be decreased by cooling CCD, and weak fluorescent image can be clearly photographed by exposure of short period.

(6) FRET (Fluorescence Resonance Energy Transfer) Method Using the Fluorescent Protein of the Present Invention The fluorescent protein of the present invention can be used for the analysis using FRET (fluorescence resonance energy transfer) method.

For example, when the fluorescent protein of the present invention is a mutant of the yellow fluorescent protein (YFP), the fluorescent protein of the present invention is used as an acceptor molecule, and the cyan fluorescent protein (CFP) is used as a donor molecule, so as to cause FRET (fluorescence resonance energy transfer) between them and enable visualization of interaction between the proteins. For example, an interaction between the proteins caused by the increase of $Ca^{2+}$ concentration (for example, binding of calcium binding protein such as calmodulin, and its target peptide such as M13) can be visualized by FRET from CFP to YFP.

Examples of a calcium-binding protein include calmodulin, troponin C, calcineurin B, myosin light chain, recoverin, S-modulin, visinin, VILIP, neurocalcin, hippocalcin, frequenin, caltractin, calpain large-subunit, S100 proteins, parvalbumin, calbindin $D_{9K}$, calbindin $D_{28K}$, and calretinin.

The amino acid sequence of a target peptide of a calcium-binding protein can be suitably selected by a person skilled in the art. For example, in the case where the calcium-binding protein is calmodulin, an amino acid sequence of a calmodulin-binding domain, which is known to exist in various proteins and peptides known to be target substances of calmodulin, can be present at the N-terminus of a fused fluorescent protein of the present invention. Currently, over 1,200 types of amino acid sequence of calmodulin-binding domain are known, and it is possible to search for these on a calmodulin binding domain database (at the website calcium.oci.utoronto.a/ctdb).

As mentioned above, the fluorescent protein of the present invention can be used for measuring intracellular calcium ion concentration or monitoring calcium ion distribution.

(7) Kit of the Present Invention

According to the present invention, there is provided a kit for analyzing localization of intracellular components and/or analyzing a physiologically active substance, which comprises at least one selected from the fluorescent protein, the fused fluorescent protein, DNA, the recombinant vector or the transformant as mentioned herein. The kit of the present invention can be prepared by known materials and techniques which are conventionally used in the art.

The reagent such as the fluorescent protein and DNA can be prepared in a form suitable for preservation by dissolving it in a suitable solvent. Examples of a suitable solvent include water, ethanol, various buffer solutions, and the like.

The present invention is illustrated by the following Examples, but the present invention is not limited by the Examples.

EXAMPLE (1) Experimental Procedures

Random Mutagenesis on Pericam

Random mutations were introduced in the gene for the circularly permuted YFP (H148D/V163A/S175G/Y203F) (Nagai, T. et al. (2001) Proc. Natl. Acad. Sci. USA 98, 3197-3202) using the error-prone PCR method. The PCR products were digested with PstI and KpnI, and subcloned into the pRSET$_B$ (Invitrogen) that carried genes for M13 and calmodulin at the Bam-HI/PstI and KpnI/EcoRI sites, respectively. Fluorescence of the bacterial colonies grown at 37° C. on a plate was analyzed using our home-made fluorescence image analyzing system (Sawano, A. et al. (2000). Nucleic Acids Research 28, e78).

Gene Construction

Oligonucleotide-directed mutageneses were performed employing the novel protocol that we reported previously (Sawano, A. et al. (2000). Nucleic Acids Research 28, e78) for mutations F46L and F64L/M153T/V163A/S175G. Using the cDNA of EYFP in pRSET$_B$ (pRSET$_B$/EYFP) as a starting material, pRSET$_B$/SEYFP, pRSET$_B$/EYFP-F46L, and pRSET$_B$/SEYFP-F46L (=pRSET$_B$/Venus) were created. The EGFP gene in pEGFP-N1-NPY (kindly provided by Dr. W. Almers) was replaced with the Venus gene to yield pVenus-N1-NPY, which encodes the NPY-Venus chimera protein. Venus was substituted for EYFP-V68L/Q69K in the gene for yellow cameleon-3.1 (YC3.1) to create YC3.12 gene, which was then subcloned into pRSET$_B$ and pCS2 for bacterial and mammalian expression, respectively.

Measurement of Fluorescence of Proteins in E. Coli

Samples of bacteria [JM109 (DE3)] were grown at 37° C. in LB containing 50 µg/ml ampicillin, harvested and resuspended in PBS to a final $OD_{600}$ of 0.5. Fluorescence spectra were taken by excitation at 485 nm for ratiometric-pericam and YFP variants, and at 435 nm for cameleon variants.

Protein Expression, In Vitro Spectroscopy, and pH— and Chloride Titrations

Proteins were expressed in E. coli, purified and spectroscopically characterized as previously described (Miyawaki, A et al., (1999) Proc.Natl.Acad.Sci.USA 96, 2135-2140). The quantum yields of YFP mutants were determined by comparison to that of fluorescein (0.91). For calculation of molar extinction coefficients, protein concentrations were measured using Bradford kit (Bio Rad) with bovine serum albumin as the standard. pH titrations were performed as described (Nagai T. et al., (2001) Proc.Natl.Acad.Sci. USA 98, 3197-3202), except that all buffers contained 35 mM [Cl$^-$] with adjustment of the ionic strength to 150 mM using potassium D-gluconate. Chloride titration was done at pH 7.0. Proteins were dissolved in 10 mM MOPS (pH 7.0) containing specified [Cl$^-$] ranging from 0 to 400 mM and the ionic strength was adjusted to 400 mM with potassium D-gluconate.

Refolding and Reoxidation of YFP Variants In Vitro

Fluorescence recovery experiments were performed as described (Reid, B. G., et al., (1997) Biochemistry 36, 6786-6791). Denatured YFPs were prepared by incubating proteins in a denaturation buffer (8M urea and 1 mM DTT) at 95° C. for 5 min. For preparation of denatured/reduced YFPs, 5 mM dithionite was added to the denaturation buffer. Recovery of fluorescence was initiated upon 100-fold dilution into a renaturation buffer (35 mM KCl, 2 mM MgCl$_2$, 50 mM Tris pH 7.5, 1 mM DTT) at 37° C. The emission at 530 nm was monitored by excitation at 515 nm.

Expression of NPY-Fusion Proteins in PC12 Cells

PC12 cells (RIKEN Cell Bank) were maintained in growth medium (DMEM, 10% fetal calf serum, 10% horse serum, 100 U/ml penicillin, 0.1 mg/ml streptomycin) at 37° C. in 5% $CO_2$. One day before transfection, cells were placed on glass coverslips. For imaging, the coverslips were coated with polyethyleneimine. The cells were transfected with pVenus-N1-NPY or pEGFP-N1-NPY using Lipofect Amine 2000 (Gibco BRL). Then the cells were allowed to differentiate and extend neuritis by including nerve growth factor (100 ng/ml human recombinant NGF-b chain, Calbiochem) in the medium.

Immunohistochemistry

Transfected PC12 cells were fixed for 15 min with 4% paraformaldehyde in PBS(-). Immunostaining for Venus and EGFP were performed using polyclonal antibody against GFP (MBL, Japan) and Alexa568-conjugated anti-rabbit IgG diluted in PBS containing 0.1% TritonX-100. The stained cells were observed using 470DF35 (excitation) and HQ525/50 (emission) for green fluorescence of Venus and EGFP, and 550DF30 (excitation) and 590DF35 (emission) for red fluorescence of Alexa568.

Monitoring of Secretion of NPY-Fusion Proteins

The transfected PC12 cells were incubated in physiological saline solution (145 mM NaCl, 5.6 mM KCl, 2.2 mM $CaCl_2$, 0.5 mM $MgCl_2$, 5.6 mM glucose, 15 mM HEPES, pH 7.4) at 37° C. in 5% $CO_2$. Depolarization stimulation was initiated by substituting pre-warmed High K$^+$ solution (95 mM NaCl, 56 mM KCl, 2.2 mM $CaCl_2$, 0.5 mM $MgCl_2$, 5.6 mM glucose, 15 mM HEPES, pH 7.4). Fluorescence intensities of the extracellular solution and cell lysate were measured at specified time points.

Imaging of Single Dense-Core Granules of PC12 Cells

An inverted microscope (IX-70, Olympus) was modified for evanescent-wave excitation as described (Steyer, J. A. et al. (2001) Nature Reviews Mol. Cell. Biol. 2, 268-275). The microscope was equipped with a high numerical aperture lens (UplanApo 60X NA1.45, Olympus), a dichroic mirror (505DRLP, Omega) and an illuminator for total internal reflection fluorescence microscopy (TIRFM) (U-DP, Olympus). A laser (argon, Omnichrome) and the illuminator were connected with a single-mode fiber to conduct the 488-nm laser line into the microscope. The laser line is projected into the exit pupil of the objective lens. Images were acquired through an emission filter (HQ525/50, Omega), using a 12-bit cooled CCD camera (MicroMax 1300Y/HS, Roper Scientific) controlled by MetaMorph/MetaFluor 4.0 software (Universal Imaging). The speed of image acquisition was either 30 frames/sec (2×2 binning) or 10 frames/sec (1×1 binning).

$Ca^{2+}$ Imaging in Hela Cells Using Yellow Cameleons

HeLa cells were transfected with pCS2-YC3.1 or pCS2-YC3.12 using Superfect (Qiagen), and imaged as described (Miyawaki, A., et al. (1999) Proc. Natl. Acad. Sci. USA 96, 2135-2140).

(2) Results and Discussion

F46L: a novel mutation that improves maturation of YFPs produced at 37° C.

Figure 1:
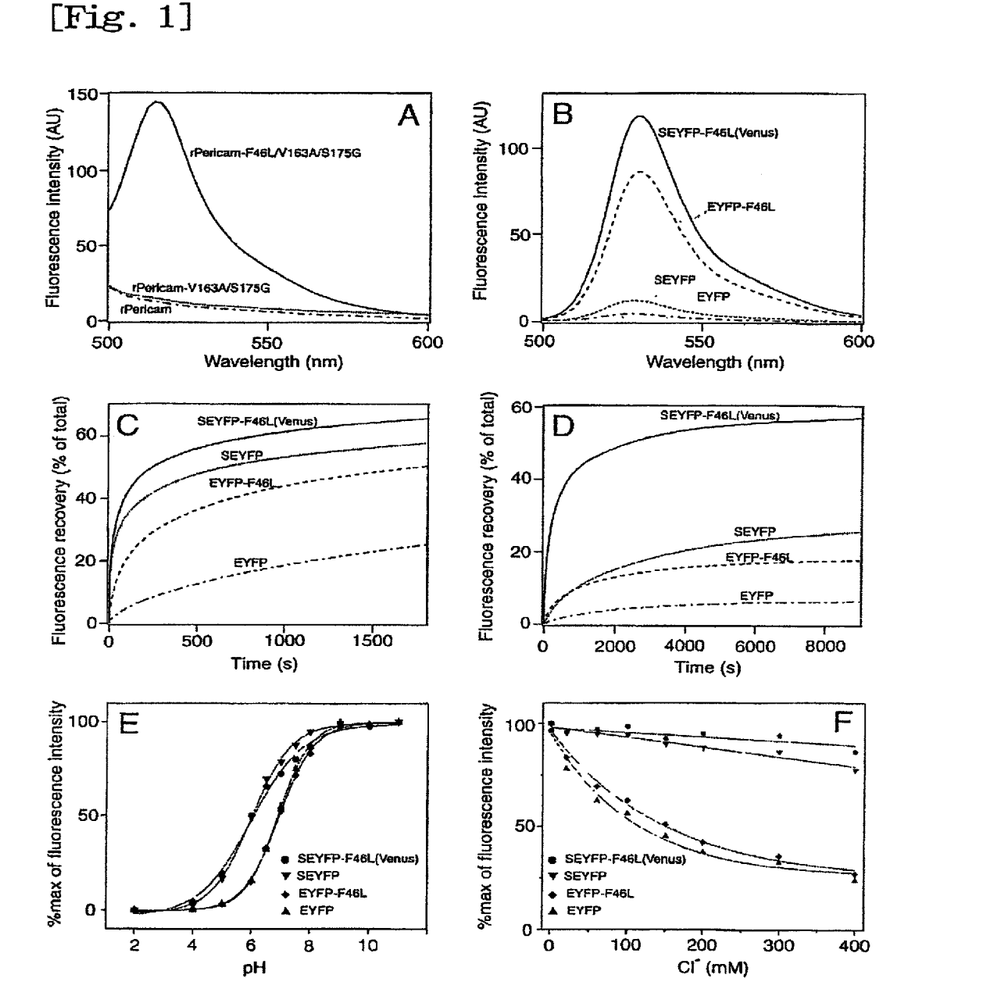
FIG. 1 shows comparative characterizations of fluorescence properties of YFP variants. (A) shows fluorescence emission spectra of ratio-metric pericams (r-pericams) produced in $E. coli$ at 37° C. (B) shows fluorescence emission spectra of YFP variants: EYFP, EYFP-F46L, SEYFP, SEYFP-F46L (Venus) produced in $E. coli$ at 37° C. (C and D) show time courses of fluorescence recovery of the four YFP variants from their denatured (C) and denatured/reduced (D) states. pH-(E) and chloride-(F) sensitivities of fluorescence of EYFP (up-triangle), EYFP-F46L (diamond), SEYFP (down-triangle), and SEYFP-F46L (=Venus) (circle), are shown.

During the random mutagenesis on pericams (circularly-permuted GFPs engineered to sense $Ca^{2+}$) (Nagai, T, et al. (2001) roc. Natl. Acad. Sci. USA 98, 3197-3202), we found several mutations that improved the maturation without affecting the $Ca^{2+}$-sensitivity. Of particular interest was a mutation of Phe-46 to Leu, which greatly improved the formation of the chromophore at 37° C. Among the three types of pericam, inverse-pericam and ratiometric-pericam that carry this F46L were found to have much more efficient maturation at 37° C. with preserving their high $Ca^{2+}$-sensitivity. FIG. 1A shows the striking effect of F46L on fluorescence development of ratiometric-pericam produced in E. coli at 37° C., whereas two other mutations, V163A and S175G, which have been identified to increase the folding efficiency had no effect. The $Ca^{2+}$-sensitivity of flash-pericam deteriorated with this mutation. Therefore, flash-pericam was made without F46L mutation, and is better produced at 28-30° C.

Since pericams are engineered from a YFP variant (EYFP-V68L/Q69K) (Miyawaki, A., et al. (1999) Proc. Natl. Acad.

Sci. USA 96, 2135-2140) to have $Ca^{2+}$-sensitivity, we were curious if F46L could increase the maturation efficiency also for YFP. The effect of F46L was studied on the most popularly used YFP variant, EYFP (S65G/S72A/T203Y). In the crystal structure of a YFP variant (S65G/S72A/V68L/T203Y) (Wachter, R. M., et al., (1999) Structure 6, 1267-1277), the benzene ring of Phe-46 neighbors on the imidazolinone, a part of the chromophore. It appears that F46L has an influence on chromophore formation of YFP. The effect of the well-known folding mutation. F64L/M153T/V163A/T203Y on EYFP was also studied along with that of F46L, since there has no report attempt to introduce those mutations to YFP variants even though they have been suggested to increase the folding efficiency in other GFP variants. By employing a protocol for multiple-site mutagenesis (Sawano, A., et al (2000) Nucleic Acids Research 28, e78), the four common folding mutations have been introduced all at once into EYFP to create SEYFP (super EYFP) (EYFP-F64L/M153T/V163A/S175G). Then EYFP-F46L and SEYFP-F46L were obtained by introducing F46L into EYFP and SEYFP, respectively. First, these four YFP variants were produced in E. coli at room temperature so that they fully matured for purification. The purified YFP variants exhibited exactly the same excitation and emission spectra, and almost equal εs and Φs, ranging from 78,700 to 101,000 $M^{-1} cm^{-1}$ and from 0.56 to 0.61, respectively (Table 1).

We next cultured the E. coli clones producing the four YFPs at 37° C., and compared fluorescence intensities of the cell suspensions (FIG. 1B). F46L greatly facilitated the maturation of YFP at 37° C. Although FIG. 1B shows the relative fluorescence intensities at one time point in a logarithmic phase, F46L gave rise to about 20-fold increase in the fluorescence of cell pellet after 12 hr incubation.

yield of recovery of EYFP and SEYFP, its effect was less potent than that of the common folding mutations. It was concluded that the mutations F64L/M153T/V163A/S175G were significantly effective in facilitating folding of YFP at 37° C.

Next, the chromophores of the urea-denatured YFPs were reduced with 5 mM dithionite (Reid, B. G. et al (1997) Biochemistry 36, 6786-6791). At 37° C., renaturation and reoxidation were initiated by dilution into buffer containing neither urea nor dithionite. Since the oxidation is the slowest step, the observed overall rate of fluorescence recovery should represent the rate of oxidation of the cyclized chromophore. The rate constants for their initial phases ($K_{ox}$s) were compared (FIG. 1D). While SEYFP and SEYFP-F46L gave similar $K_{fold}$s, the speed and yield of the renaturation from denatured/reduced protein at 37° C. was significantly improved by F46L (FIG. 1D; $K_{ox}$ values in Table 1, $2.36 \times 10^{-3} S^{-1}$ vs. $8.04 \times 10^{-3} S^{-1}$). Interestingly, this improvement was not clearly observed when the experiments were carried out at room temperature. Also EYFP-F46L showed faster reoxidation than SEYFP at 37° C. (FIG. 1D).

Recently, a new YFP named Citrine was reported, in which the mutation Q69M confers some beneficial properties. Of these is the improved maturation speed. Therefore, the maturation efficiency of the Citrine was assessed at 37° C. by the renaturation and reoxidation assay. Although Citrine could fold rapidly at same rate as Venus (Kfold values in Table 1, $6.39 \times 10^{-2} S^{-1}$), the oxidation rate was not improved (Kox values in Table 1, $2.42 \times 10^{-3} S^{-1}$).

The rate of fluorescence acquisition of YFP renatured from inclusion bodies would inform us of the kinetics of de novo maturation, including the step of cyclization of an internal tripeptide (Reid, B. G. et al (1997) Biochemistry 36, 6786-

TABLE 1

Spectral characterization of YFP mutants

| Name | Substitutions | λabs (ε) | λem (Φ) | pKa | Kd for Cl (mM) | kfold ($10^{-2} s^{-1}$) | Kox ($10^{-3} s^{-1}$) | Relative fluorescence at 37° C. |
|---|---|---|---|---|---|---|---|---|
| EYFP | — | 515 (80.4) | 528 (0.61) | 6.9 | 110 | 0.39 | 2.53 | 1 |
| Citrine | Q69M | ND | ND | 6.0 | >$10^4$ | 6.39 | 2.42 | ND |
| EYFP-F46L | F46L | 515 (78.7) | 528 (0.61) | 6.9 | 145 | 1.94 | 3.87 | 20 |
| SEYFP | F64L/M153T/V163A/S175G | 515 (101) | 528 (0.56) | 6.0 | >$10^4$ | 6.60 | 2.36 | 3 |
| SEYFP-F46L (Venus) | F46L/F64L/M153T/V163A/S175G | 515 (92.2) | 528 (0.57) | 6.0 | >$10^4$ | 5.62 | 8.04 | 30 |

Venus: the Best Maturation Version of YFP at 37° C.

The folding efficiency was assessed at 37° C. by monitoring the acquisition of fluorescence upon renaturation of urea-denatured protein with a mature chromophore (Reid, B. G. et al (1997) Biochemistry 36, 6786-6791). As the protein refolds, the matured chromophore is buried inside the (β-barrel of GFP, resulting in recovery of fluorescence (FIG. 1C). The yield of the fluorescence recovery for EYFP was less than 30% as judged from the intensity of the fluorescence before denaturation, suggesting formation of a great deal of insoluble aggregates through the denaturation procedure. The renaturation of all the YFP variants proceeded through two distinct kinetic phases as previously reported (Reid, B. G. et al (1997) Biochemistry 36, 6786-6791). The first-order rate constants for the initial phase varied among the YFP variants (Table 1). Both SEYFP and SEYFP-F46L, containing the mutations F64L/M153T/V163A/S175G, recovered very fast with rate constants ($K_{fold}$s) of $6.60 \times 10^{-2} S^{-1}$ and $5.62 \times 10^{-2}$ respectively. Although F46L alone increased the speed and 6791). However, SEYFP and SEYFP-F46L were hardly isolated from the insoluble pellets after cell lysis. Although the effect of F46L on the cyclization was not examined, the above results indicate that F46L accelerates the oxidation step, leading to the enhancement of fluorescence development of YFP at 37° C. Presumably, the side chain of Leu-46 promotes not only oxygen accessibility but also folding of nascent protein into a crucial but unidentified conformational state that is favorable for the oxidation reaction. This argument is consistent with the fact F46L alone facilitated the refolding of urea-denatured protein (FIG. 1C). In this respect, the folding and chromophore formation should be considered to occur cooperatively.

SEYFP-F46L folds and forms the chromophore very efficiently at 37° C., giving the brightest yellowish light. This new variant is herein referred to as "Venus".

Less Sensitivity of Venus to Proton and Chloride Ions

The protonation and Cl⁻ binding of the chromophore of YFP are positively cooperative (Wachter, R. M., et al. (2000)

J. Mol. Biol. 301, 157-171). Thus, the sensitivity of the 4 YFP variants to $H^+$ and $Cl^-$ was examined. For pH titration, the buffers containing 35 mM of $[Cl^-]$ (concentration of $Cl^-$) were used. The pH titration curves are shown in FIG. 1E. The pKa of EYFP was 6.9, indicating that quantitative measurement of its fluorescence in living cells may suffer from pH-related artifacts. Adding the mutation F46L did not change the pH-sensitivity of EYFP. On the other hand, SEYFP and Venus gave titration curves with a pKa of 6.0. It was therefore concluded that some mutations of F64L/M153T/V163A/S175G decreased the pH-sensitivity of YFP.

FIG. 1F shows the dependence of fluorescence of the YFPs with increasing $[Cl^-]$ at pH 7.0. EYFP and EYFP-F46L were sensitive to $Cl^-$ with the Kd values of 110 mM and 145 mM, respectively. By contrast, SEYFP and Venus were less sensitive to the anion. Within the range of physiological $[Cl^-]$ (below 150 mM) at pH 7.0, their fluorescence was not affected. Thus, the introduction of mutations F64L/M153T/V163A/S175G was effective in removing the $Cl^-$ sensitivity. Among the mutations, V163A appears to be critical because the side chain of Val163 has been shown to participate in lining the anion binding cavity of a variant of YFP (Wachter, R. M., et al (2000) J. Mol. Biol. 301, 157-171).

Decreasing pH lowers the absorbance of YFP at 511 nm. Also, $Cl^-$ decreased the absorbance of YFP without affecting the Φ; there is no evidence for collisional quenching of YFP fluorescence by $Cl^-$ (Wachter, R. M., et al. (2000) J. Mol. Biol. 301, 157-171). YFP has often been used as an acceptor for FRET in combination with CFP as a donor (Tsien, R. Y. et al. (1998) Science 280, 1954-1955). Since the absorbance of an acceptor is one of the critical factors that determine FRET efficiency, the pH and $Cl^-$ sensitivity of YFP should be minimized for obtaining reliable signals of FRET (Miyawaki, A. and Tsien, R. Y. (2000) Methods Enzymol. 327, 472-500). Even aside from the maturation efficiency, Venus should be more suitable as a FRET acceptor than EYFP.

Taken altogether, Venus is brighter than EYFP, the most common YFP, through the effects exerted by two kinds of mutations: i) enhanced maturation of chromophore at 37° C. by the mutation F46L, and ii) enhanced folding at 37° C. and reduced quenching by $H^+$ and $Cl^-$ by a set of mutations F64L/M153T/V163A/S175G.

Fluorescent Labeling of Secretory Dense-Core Granules in PC12 Cells with Venus

Secretory organelles have acidic environment and mostly dense-core protein matrix. Thus, fluorescent labeling of the organelles with GFP is relatively difficult. Although GFP mutants with improved optical and maturation properties, such as EGFP (enhanced GFP, Clontech) were successfully targeted to dense-core secretory granules of PC12 cells (Lang, T., et al. (1997) Neuron 18, 857-863) and large dense-core secretory vesicles of INS-1 β cells (Tsuboi, T., et al (2000) Curr. Biol. 10, 1307-1310), imperfect colocalization of the GFP's fluorescence with some specific markers for the organelles was noticed, which suggested mistargeting of the recombinant fluorescent protein and non-fluorescence of the protein in the organelles.

In this example, we constructed a mammalian expression plasmid coding for Venus fused to the C-terminus of neuropeptide Y (NPY), producing NPY-Venus. The performance of the chimeric protein was examined in comparison with that of NPY-EGFP, in view of the following two points. The first point is how specifically is the NPY-fusion protein targeted to secretory dense-core granules. The second point is how efficiently does the correctly-targeted NPY-fusion protein fluoresce.

Figure 2:
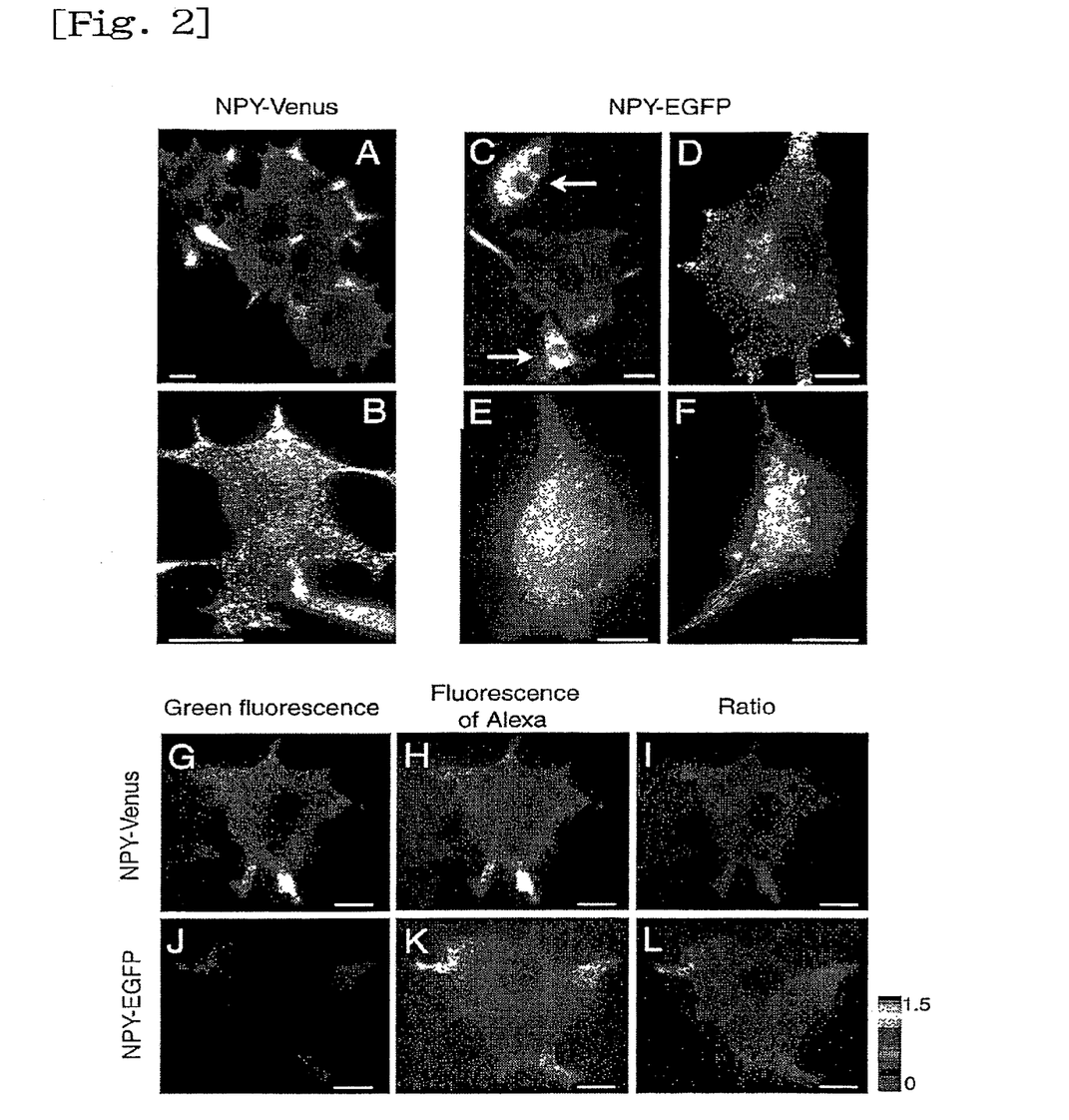

The transfected PC12 cells were allowed to differentiate and extend neurites by treatment with nerve growth factor (NGF). FIG. 2A shows a wide-view fluorescence micrograph of 6 cells expressing NPY-Venus. A typical high magnification image is shown in FIG. 2B. Bright and punctate fluorescence from NYP-Venus was observed to be concentrated in the neurites, which were rich in dense-core granules, indicating correct targeting of NPY-Venus. It should be noted that nearly all the fluorescent cells expressing NPY-Venus on a coverslip showed a similar fluorescence pattern. By contrast, the PC12 cells expressing NPY-EGFP displayed three distinct patterns. About 60% of the fluorescent cells had bright neurites (FIG. 2C, the middle cell), and the punctate fluorescence pattern was confirmed by a high magnification micrograph (FIG. 2D). The remaining 40% of cells showed a hazy fluorescence over the entire cytosol with bright reticular spots (FIG. 2C, indicated by arrows; FIG. 2E) or tubular objects (FIG. 2F), indicative of mistargeting of NPY-EGFP. Possibly aberrant folding of EGFP affected the proper processing of the neuropeptide.

Although the correctly-targeted NPY-EGFP gave detectable fluorescence, the intensity was about 10-times lower than that of NPY-Venus; the exposure times for image acquisition were 100 msec for FIG. 2B and 1.5 sec for FIG. 2D. The brightness of the granules containing NPY-Venus was due to either the improved maturation yield of Venus or the abundance of NYP-Venus in the granules. To distinguish between the two possibilities, the amount of the recombinant proteins correctly-targeted to the dense-core granules was quantified immunohistochemically. The PC12 cells transfected with pVenus-N1-NPY and pEGFP-N1-NPY were fixed and subjected to immunostaining using an anti-GFP antibody and an Alexa562-conjugated secondary antibody. The green fluorescence signals from Venus and EGFP were captured through a common filter set for GFP observation (FIGS. 2G and 2J, respectively), and red fluorescence of Alexa562 was detected through another filter set (FIGS. 2H and 2K). The images of FIGS. 2G and 2J or FIGS. 2H and 2K were taken under the same optical condition and are displayed in the same grey scale. Despite similar amount of the recombinant proteins (FIGS. 2H and 2K), the fluorescence of Venus was clearly visualized (FIG. 2G), whereas that of EGFP was hardly detected (FIG. 2J). Fluorescence intensities per recombinant protein molecules are shown in pseudo-colored ratio images (FIGS. 2I and 2L), which were obtained by dividing the green fluorescence signals by the immunofluorescence signals. These results indicate that Venus can mature to be fluorescent more efficiently in dense-core granules than EGFP.

Efficient Monitoring and Dynamic Visualization of Secretion of NPY-Venus

Figure 3:
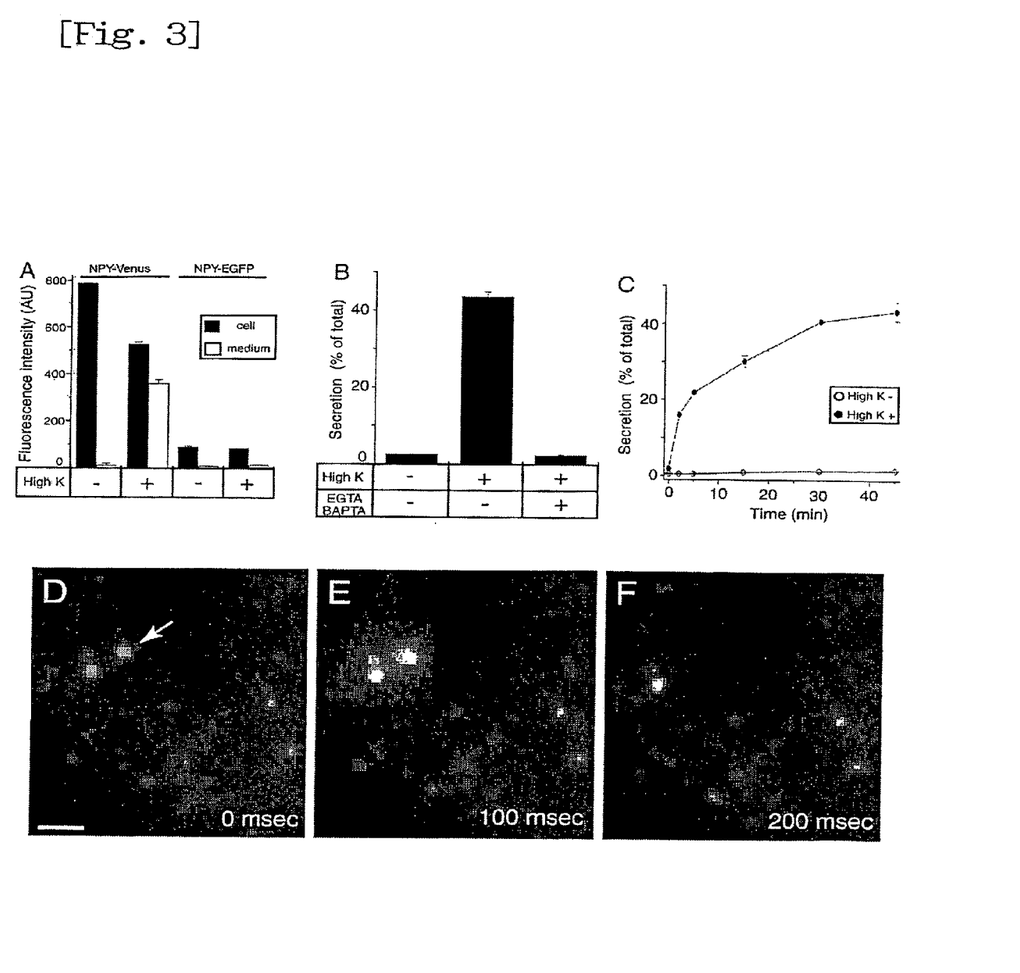
FIG. 3 shows observation of exocytototic events. (A) shows intensitites of fluorescence of NPY-Venus or NPY-EGFP recovered from cultured PC12 cells (filled bars) and the medium (open bars) with or without depolarization (High K$^-$) stimulation. (B) shows $Ca^{2+}$-dependency of the NPY-Venus secretion induced by depolarization stimulation. (C) shows time courses of the accumulation of NPY-Venus in the medium with and without depolarization simulation. (D-F) show secretion of a single dense-core granule (indicated by an arrow in D) visualized with NPY-Venus. Images were captured consecutively every 100 msec. Scale bar, 10 μm.

NPY-Venus has enabled two experiments for understanding of exocytosis of dense-core granules of PC 12 cells. First, depolarization-induced secretion of NPY-Venus was monitored by measuring the increase in fluorescence of medium as well as the loss in cellular fluorescence (FIG. 3A), because NPY-Venus gave specific and strong labeling of dense-core granules of a large population of cultured PC12 cells. Such a population assay was hardly possible with the use of proinsulin-GFP as reported previously (Angleson, J. K. et al (1997) Trends Neurosci. 20, 281-187). In contrast to conventional biochemical or electrophysiological approaches (Angleson, J. K. et al (1997) Trends Neurosci. 20, 281-187), the measurement of fluorescence of secreted NPY-Venus in the medium allows simple, fast and efficient monitoring of exocytosis of PC12 cells. Thirty minutes after the depolarization, the amount of the secreted NPY-Venus reached about 40% of total, and this secretion was prevented when both extra- and intra-cellular $Ca^{2+}$ was chelated with EGTA and BAPTA-AM (FIG. 3B). Temporal profile of the secretion was also easily obtained, which revealed that 50% of the secretion occurred within initial 5 minutes (FIG. 3C).

Second, dynamics of small single fluorescent dense-core granules was observed in NGF-treated PC12 cells with high temporal and spatial resolutions using evanescent-wave microscopy. A similar evanescent-wave field fluorescence imaging was performed using a GFP mutant (GFPmut2) fused to human chromogranin B (Lang, T., et al., (1997) Neuron 18, 857-863). However, they observed large granules (~0.5 µm in diameter) at 0.5 Hz in PC12 cells that never differentiated. In this example, by contrast, the granules were allowed to differentiate to become dense-core granules with reduced size (~0.2 µm in diameter). Owing to the bright labeling with NPY-Venus, we were able to view such small granules using a conventional cooled CCD camera at 10 Hz without binning or at video-rate (30 Hz) with binning 2. FIGS. 3D-F are consecutive images showing a single exocytotic event induced by depolarization. After docking at the plasma membrane, the fluorescence of NPY-Venus in a dense-core granule (indicated by an arrow in FIG. 3D) spouted into the medium (FIG. 3E) and then disappeared (FIG. 3F).

Immediate Detection of Signals of Fret Between CFP and Venus

Figure 4:
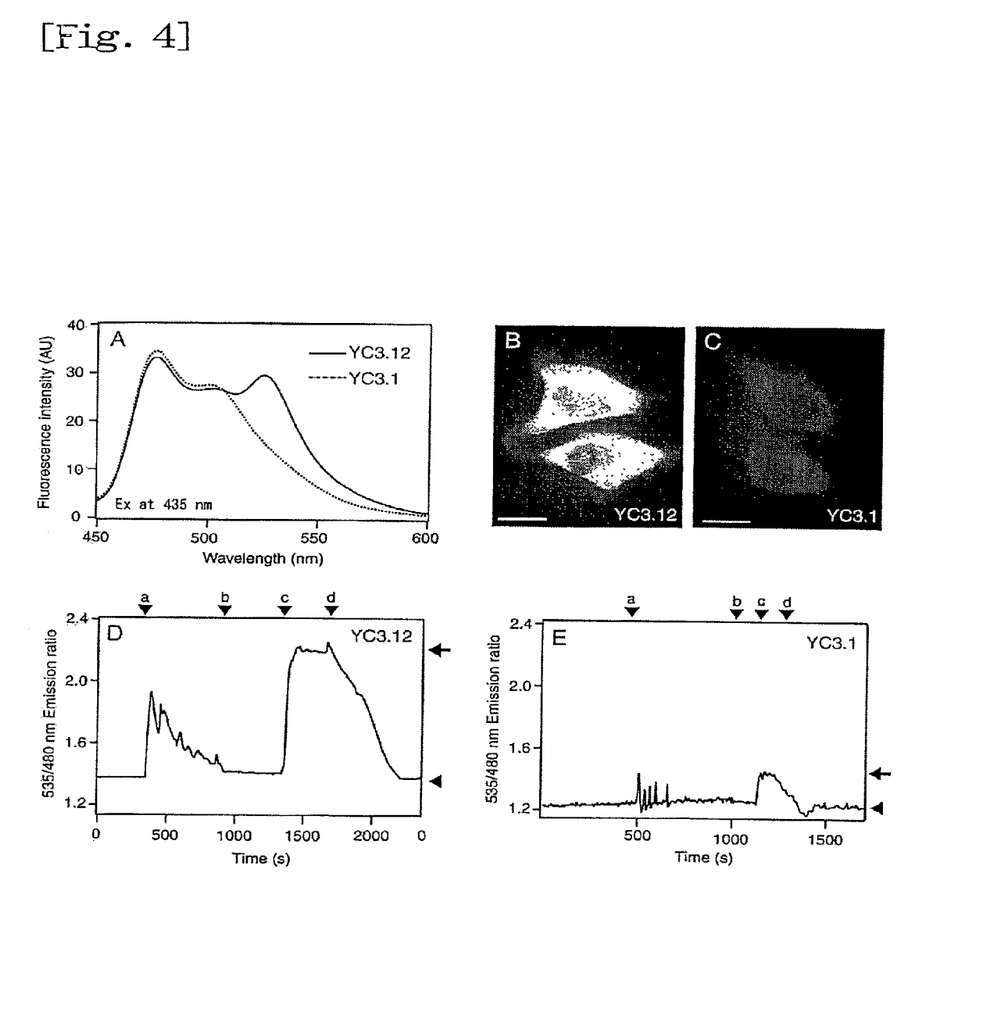
FIG. 4 shows the performance of YC3.12, the yellow cameleon containing Venus. (A) shows fluorescence emission spectra of bacteria samples producing YC3.12 and YC3.1 at 37° C. (B and C) show development of fluorescence of Venus (B) and EYFP-V68L/Q69K (C), the acceptors of YC3.12 and YC3.1, respectively. These images were taken using an excitation filter 490DFDF10 and an emission filter 535DF25 5 hrs after addition of transfection reagents. Scale bar, 10 μm. (D and E) show measurement of cytosolic free $Ca^{2+}$ concentration in HeLa cells expressing YC3.12 (D) and YC3.1 (E) for 5.0 hours. The 535 to 480 nm emission ratios were sampled every 5 seconds. The right-hand ordinate gives $R_{max}$ (an arrow) and $R_{min}$ (an arrowhead).

For FRET using GFPs, it is preferable that an acceptor GFP matures more efficiently than a donor GFP. Otherwise, excess of donor molecules would result in dilution of FRET signals by the emission from the donors that do not participate in the FRET. Yellow cameleon (YC) is a $Ca^{2+}$ indicator protein consisting of a CFP, calmodulin, a glycylglycine linker, the calmodulin-binding domain of myosin light chain kinase (M13), and YFP (Miyawaki, A., et al. (1997) Nature 388, 882-887). Although the stoichiometry of donors and acceptors is 1:1 at a gene level, EYFP-V68L/Q69K which is the acceptor of YC3.1 matures poorly at 37° C. or in certain organelles (Miyawaki, A., et al. (1999) Proc. Natl. Acad. Sci. USA 96, 2135-2140). To obtain the signal of YC efficiently in all situations, we have created YC3.12 by substituting Venus for EYFP-V68L/Q69K in YC3.1. Bacteria samples producing YC3.12 and YC3.1 were grown at 37° C., and their emission spectra with excitation at 435 nm were compared (FIG. 4A). The emission spectrum of the produced YC3.12 was equal to that of yellow cameleon which fully matures, indicating that the YC3.12 protein was qualified to work as the $Ca^{2+}$ indicator. By contrast, the YC3.1 had no mature EYFP-V68L/Q69K at 37° C. The efficient maturation of Venus in YC3.12 was verified also in HeLa cells, compared with that of EYFP-V68L/Q69K in YC3.1 (FIGS. 4B and 4C). The Venus strongly fluoresced 5 hrs after initiation of gene-transfection. Then we were interested in how soon the $Ca^{2+}$ signal of YC3.12 became detectable. After incubation of HeLa cells with cDNA and Superfect (Qiagen) reagent for only 2.5 hrs, we were able to observe a histamine-triggered $Ca^{2+}$ transient with a large dynamic range (FIG. 4D), which agrees well with the usual behavior of yellow cameleon (Miyawaki, A., et al. (1999) Proc. Natl. Acad. Sci. USA 96, 2135-2140). In contrast, YC3.1 gave only poor signals under the same conditions (FIG. 4E). The use of YC3.12 exempts us from the time constraint, allowing quick detection of $Ca^{2+}$ signals from, for example, fresh neuronal cells in acute slices of mouse or rat brain after ballistic particle-mediated gene transfer

INDUSTRIAL APPLICABILITY

According to the present invention, there are provided novel GFP or YEP mutants having an excellent maturation efficacy and having a decreased sensitivity to both of $H^+$ and $Cl^-$.

The invention claimed is:

1. An isolated nucleic acid molecule comprising a nucleic acid sequence encoding a fluorescent protein, the fluorescent protein comprising:
   (a) the amino acid sequence of SEQ ID NO:1; or
   (b) an amino acid sequence having a deletion, substitution, and/or addition of one to twenty amino acids in the amino acid sequence of SEQ ID NO: 1 and having the same or decreased sensitivity to $H^+$ or $Cl^-$ than that of a protein having the amino acid sequence of SEQ ID NO: 1, wherein leucine at position 47, leucine at position 65, threonine at position 154, alanine at position 164, and glycine at position 176 are maintained.

2. The nucleic acid molecule of claim 1, wherein the fluorescent protein comprises the amino acid sequence of (b) having a deletion, substitution, and/or addition of one to ten amino acids in the amino acid sequence of SEQ ID NO: 1.

3. The nucleic acid molecule of claim 1, wherein the nucleic acid sequence encodes a fusion protein comprising the fluorescent protein fused with another protein.

4. The nucleic acid molecule of claim 3, wherein the another protein is a protein which localizes to an intracellular organelle.

5. The nucleic acid molecule of claim 3, wherein the another protein is a protein that targets a calcium binding protein.

6. A recombinant vector comprising the nucleic acid molecule of claim 1.

7. The recombinant vector of claim 6, wherein the nucleic acid molecule further comprises expression control sequences operatively linked to the nucleic acid sequence.

8. A recombinant host cell comprising the nucleic acid molecule of claim 1.

9. A recombinant host cell comprising the recombinant vector of claim 7.

10. An isolated nucleic acid molecule comprising a nucleic acid sequence encoding a fluorescent protein, the fluorescent protein comprising a mutant of the amino acid sequence of SEQ ID NO:1,
    wherein the mutant fluorescent protein has leucine at positions 47 and 65, alanine at position 73, threonine at position 154, alanine at position 164, glycine at position 176, and tyrosine at position 204, wherein the mutant fluorescent protein has an amino acid sequence having deletion, substitution, and/or addition of one to twenty amino acids in the amino acid sequence of SEQ ID NO: 1, and wherein the mutant fluorescent protein has a fluorescence intensity that is equivalent to a protein with the amino acid sequence of SEQ ID NO: 1 and exhibits a yellow emission color.

11. The nucleic acid molecule of claim 10, wherein the mutant fluorescent protein has an amino acid sequence having a deletion, substitution, and/or addition of one to ten amino acids in the amino acid sequence of SEQ ID NO: 1.

12. The nucleic acid molecule of claim 10, wherein the nucleic acid sequence encodes a fusion protein comprising the fluorescent protein fused with another protein.

13. The nucleic acid molecule of claim 12, wherein the another protein is a protein which localizes to an intracellular organelle.

14. The nucleic acid molecule of claim 12, wherein the another protein is a protein that targets a calcium binding protein.

15. A recombinant vector comprising the nucleic acid molecule of claim 10.

16. The recombinant vector of claim 15, wherein the nucleic acid molecule further comprises expression control sequences operatively linked to the nucleic acid sequence.

17. A recombinant host cell comprising the nucleic acid molecule of claim 10.

18. A recombinant host cell comprising the recombinant vector of claim 16.

19. A kit for analyzing localization of intracellular components and/or analyzing a physiologically active substance, which kit comprises a nucleic acid molecule comprising a nucleic acid sequence encoding a fluorescent protein, wherein the fluorescent protein comprises:
    (a) the amino acid sequence of SEQ ID NO: 1;
    (b) an amino acid sequence having a deletion, substitution, and/or addition of one to twenty amino acids in the amino acid sequence of SEQ ID NO: 1 and having the same or decreased sensitivity to $H^+$ or $Cl^-$ than that of a protein having the amino acid sequence of SEQ ID NO:

1, wherein leucine at position 47, leucine at position 65, threonine at position 154, alanine at position 164, and glycine at position 176 are maintained; or (c) a fusion protein comprising the fluorescent protein of (a) or (b) and another protein.

20. The kit of claim 19, wherein a recombinant vector comprises the nucleic acid molecule.

21. A kit for analyzing localization of intracellular components and/or analyzing a physiologically active substance, which kit comprises the nucleic acid molecule of claim 10.

22. The kit of claim 21, wherein a recombinant vector comprises the nucleic acid molecule.

* * * * *

SEQUENCE LISTING

```
<160> NUMBER OF SEQ ID NOS: 6

<210> SEQ ID NO 1
<211> LENGTH: 239
<212> TYPE: PRT
<213> ORGANISM: Artificial Sequence
<220> FEATURE:
<223> OTHER INFORMATION: Recombinant Fluorescent Proteins Based on
      Aequora Victoria Sequences

<400> SEQUENCE: 1

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Leu Ile
        35                  40                  45

Cys Thr Thr Gly Lys Leu Pro Val Pro Trp Pro Thr Leu Val Thr Thr
    50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110
```

```
Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
                180                 185                 190

Pro Val Leu Leu Pro Asp Asn His Tyr Leu Ser Tyr Gln Ser Ala Leu
                195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235
```

```
<210> SEQ ID NO 2
<211> LENGTH: 239
<212> TYPE: PRT
<213> ORGANISM: Artificial Sequence
<220> FEATURE:
<223> OTHER INFORMATION: Recombinant Fluorescent Proteins Based on
      Aequora Victoria Sequences

<400> SEQUENCE: 2

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
                180                 185                 190

Pro Val Leu Leu Pro Asp Asn His Tyr Leu Ser Thr Gln Ser Ala Leu
                195                 200                 205

Ser Lys Asp Pro Asn Glu Lys Arg Asp His Met Val Leu Leu Glu Phe
210                 215                 220

Val Tyr Ala Ala Gly Ile Thr Leu Gly Met Asp Glu Leu Tyr Lys
225                 230                 235
```

<210> SEQ ID NO 3
<211> LENGTH: 239
<212> TYPE: PRT
<213> ORGANISM: Artificial Sequence
<220> FEATURE:
<223> OTHER INFORMATION: Recombinant Fluorescent Proteins Based on Aequora Victoria Sequences

<400> SEQUENCE: 3

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 4
<211> LENGTH: 720
<212> TYPE: DNA
<213> ORGANISM: Artificial Sequence
<220> FEATURE:
<223> OTHER INFORMATION: DNA Encoding Recombinant Fluorescent Proteins Based on Aequora Victoria Sequences

<400> SEQUENCE: 4

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt gatctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctgggcac      420
```
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagtaa    720

<210> SEQ ID NO 5
<211> LENGTH: 720
<212> TYPE: DNA
<213> ORGANISM: Artificial Sequence
<220> FEATURE:
<223> OTHER INFORMATION: DNA Encoding Recombinant Fluorescent Proteins
      Based on Aequora Victoria Sequences

<400> SEQUENCE: 5
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccttcggcta cggcctgcag tgcttcgccc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctgggghcac    420 aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagct accagtccgc cctgagcaaa gaccccaacg agaagcgcga tcacatggtc    660
ctgctggagt tcgtgaccgc cgccgggatc actctcggca tggacgagct gtacaagtaa    720

<210> SEQ ID NO 6
<211> LENGTH: 239
<212> TYPE: PRT
<213> ORGANISM: Artificial Sequence
<220> FEATURE:
<223> OTHER INFORMATION: Recombinant Fluorescent Proteins Based on
      Aequora Victoria Sequences

<400> SEQUENCE: 6

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

```
Ile Asp Phe Lys Glu Asp Gly Asn Ile Leu Gly His Lys Leu Glu Tyr
    130             135             140
Asn Tyr Asn Ser His Asn Val Tyr Ile Met Ala Asp Lys Gln Lys Asn
145             150             155                         160
Gly Ile Lys Val Asn Phe Lys Ile Arg His Asn Ile Glu Asp Gly Ser
                165             170             175
Val Gln Leu Ala Asp His Tyr Gln Gln Asn Thr Pro Ile Gly Asp Gly
            180             185             190
Pro Val Leu Leu Pro Asp Asn His Tyr Leu Ser Tyr Gln Ser Ala Leu
        195             200             205
Ser Lys Asp Pro Asn Glu Lys Arg Asp His Met Val Leu Leu Glu Phe
    210             215             220
Val Thr Ala Ala Gly Ile Thr Leu Gly Met Asp Glu Leu Tyr Lys
225             230             235
```